(12) United States Patent
Maschke

(10) Patent No.: US 9,237,919 B2
(45) Date of Patent: Jan. 19, 2016

(54) CRYOCATHETER FOR INTRODUCTION INTO A BODY VESSEL TOGETHER WITH MEDICAL INVESTIGATION AND TREATMENT EQUIPMENT

(75) Inventor: Michael Maschke, Lonnerstadt (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 1813 days.

(21) Appl. No.: 11/583,447

(22) Filed: Oct. 19, 2006

(65) Prior Publication Data

US 2007/0093710 A1  Apr. 26, 2007

(30) Foreign Application Priority Data

Oct. 20, 2005  (DE) .......................... 10 2005 050 344

(51) Int. Cl.
*A61B 18/02* (2006.01)
*A61B 5/00* (2006.01)
(Continued)

(52) U.S. Cl.
CPC ............... *A61B 18/02* (2013.01); *A61B 5/0066* (2013.01); *A61B 5/6852* (2013.01); *A61B 5/6853* (2013.01); *A61B 8/12* (2013.01); *A61B 8/445* (2013.01); *A61B 8/5238* (2013.01); *A61M 25/10* (2013.01); *A61B 5/721* (2013.01); *A61B 6/12* (2013.01); *A61B 6/5247* (2013.01); *A61B 2017/22051* (2013.01);
(Continued)

(58) Field of Classification Search
CPC ............. A61B 2018/0212; A61B 2018/00988; A61B 2018/0022

USPC .......................................................... 600/407
See application file for complete search history.

(56) References Cited

U.S. PATENT DOCUMENTS 4,684,370 A * 8/1987 Barrett ........................ 623/16.11
5,209,725 A * 5/1993 Roth ............................. 604/508
(Continued)

FOREIGN PATENT DOCUMENTS

DE      198 27 460 A1    12/1998
DE      19852441 A1       7/1999
(Continued)

OTHER PUBLICATIONS

James D. Joye and Kristine Tatsutani; "In Vivo Study of Endovascular Cryotherapy for the Prevention of Restenosis"; pp. 1-4.
(Continued)

*Primary Examiner* — Long V Le
*Assistant Examiner* — Saurel J Selkin

(57) ABSTRACT

A cryocatheter for introduction into a body vessel or into an organ, with a catheter inner surrounded by a catheter sheath, and with a catheter tip arranged at its distal end, with a feed line for an expansion or cooling agent arranged in the catheter sheath or the catheter inner, and with a balloon, arranged close to the catheter tip, which can be expanded and contracted again by means of the expansion and cooling agent, is to be constructed in such a way that by simple manipulation it can be positioned at a precise target position in the body vessel and, in addition, it minimizes the burden on the patient from invasive interventions. For this purpose, in accordance with the invention an image capture device, with at least one imaging sensor for mapping the region of the vessel around the balloon, is positioned in the region of the catheter tip.

12 Claims, 11 Drawing Sheets

(51) Int. Cl.
*A61B 8/12* (2006.01)
*A61B 8/08* (2006.01)
*A61M 25/10* (2013.01)
*A61B 8/00* (2006.01)
*A61B 6/12* (2006.01)
*A61B 6/00* (2006.01)
*A61B 17/22* (2006.01)
*A61B 18/00* (2006.01)
*A61B 19/00* (2006.01)
*A61M 25/00* (2006.01)
*A61M 25/06* (2006.01)

(52) U.S. Cl.
CPC .............. *A61B 2018/0022* (2013.01); *A61B 2018/00988* (2013.01); *A61B 2018/0212* (2013.01); *A61B 2018/0262* (2013.01); *A61B 2019/448* (2013.01); *A61B 2019/5236* (2013.01); *A61B 2019/5278* (2013.01); *A61B 2019/5429* (2013.01); *A61B 2019/5475* (2013.01); *A61M 25/0082* (2013.01); *A61M 2025/0681* (2013.01)

(56) References Cited

U.S. PATENT DOCUMENTS

| | | | |
|---|---|---|---|
| 5,522,882 A * | 6/1996 | Gaterud et al. | 623/1.11 |
| 5,544,660 A * | 8/1996 | Crowley | 600/466 |
| 5,599,324 A * | 2/1997 | McAlister et al. | 604/523 |
| 5,606,981 A * | 3/1997 | Tartacower et al. | 600/585 |
| 5,752,513 A | 5/1998 | Gasparakis | |
| 5,921,926 A | 7/1999 | Rolland et al. | |
| 5,976,107 A * | 11/1999 | Mertens et al. | 604/164.13 |
| 6,203,493 B1 * | 3/2001 | Ben-Haim | 600/117 |
| 6,283,959 B1 * | 9/2001 | Lalonde et al. | 606/21 |
| 6,309,370 B1 * | 10/2001 | Haim et al. | 604/66 |
| 6,355,029 B1 | 3/2002 | Joye et al. | |
| 6,377,048 B1 | 4/2002 | Alexandrowicz | |
| 6,471,693 B1 * | 10/2002 | Carroll et al. | 606/21 |
| 6,506,972 B1 | 1/2003 | Wang | |
| 6,661,240 B1 | 12/2003 | Bhatt | |
| 6,704,594 B1 | 3/2004 | Blank et al. | |
| 6,772,001 B2 | 8/2004 | Maschke | |
| 2002/0163994 A1 | 11/2002 | Jones | |
| 2003/0130650 A1 * | 7/2003 | Yaron | 606/21 |
| 2004/0037455 A1 * | 2/2004 | Klingensmith et al. | 382/128 |
| 2004/0100557 A1 | 5/2004 | Harris | |
| 2004/0148005 A1 * | 7/2004 | Heuser | 623/1.11 |
| 2004/0167505 A1 | 8/2004 | Joye et al. | |
| 2005/0038421 A1 | 2/2005 | Joye et al. | |
| 2005/0101859 A1 | 5/2005 | Maschke | |
| 2005/0113685 A1 | 5/2005 | Maschke et al. | |
| 2005/0192496 A1 | 9/2005 | Maschke | |

FOREIGN PATENT DOCUMENTS

| | | |
|---|---|---|
| DE | 19852467 A1 | 7/1999 |
| DE | 20009204 U1 | 8/2000 |
| DE | 10253634 A1 | 5/2004 |
| DE | 103 43 808 A1 | 5/2005 |
| DE | 103 54 496 A1 | 7/2005 |
| DE | 10 2004 001 498 A1 | 8/2005 |
| EP | 1034738 B1 | 9/2004 |
| WO | WO 0111409 A2 | 2/2001 |
| WO | WO 2004110258 A2 | 12/2004 |

OTHER PUBLICATIONS

Endovaskuläre Brachytherapie in der Restenoseprophylaxe nach Angioplastie und Stentimplantation; Wohlgemut W.A., Bohndorf K.; Endovaskuläre Brachytherapie in der Restenoseprophylaxe nach Angioplastie und Stentimplantation; Fortsch. Röntgenstr 2003; 175: 246-252; 2003.

Miniature ultrasonic probe construction for minimal access surgery R.J. Dickinson and R. I. Kitney;; Dickinson et al.; Miniature ultrasonic probe construction for minimal access surgery Department of Bioengineering, Imperial College, London; Institute of Physics Publishing; Physics in Medicine and Biology Phys. Med. Biol. 49 (2004) Seiten 3527 bis 3538; 2004; Aug. 2, 2004.

Yamamoto N. et al; "Nonfluoroscopic Guidance for Catheter Placement into the Coronary Sinus under Direct Vision Using a Balloon-Tipped Cardioscope"; Pacing and Clinical Electrophysiology; vol. 21; No. 9; pp. 1724-1729; 1998; Sep. 1, 1998.

* cited by examiner

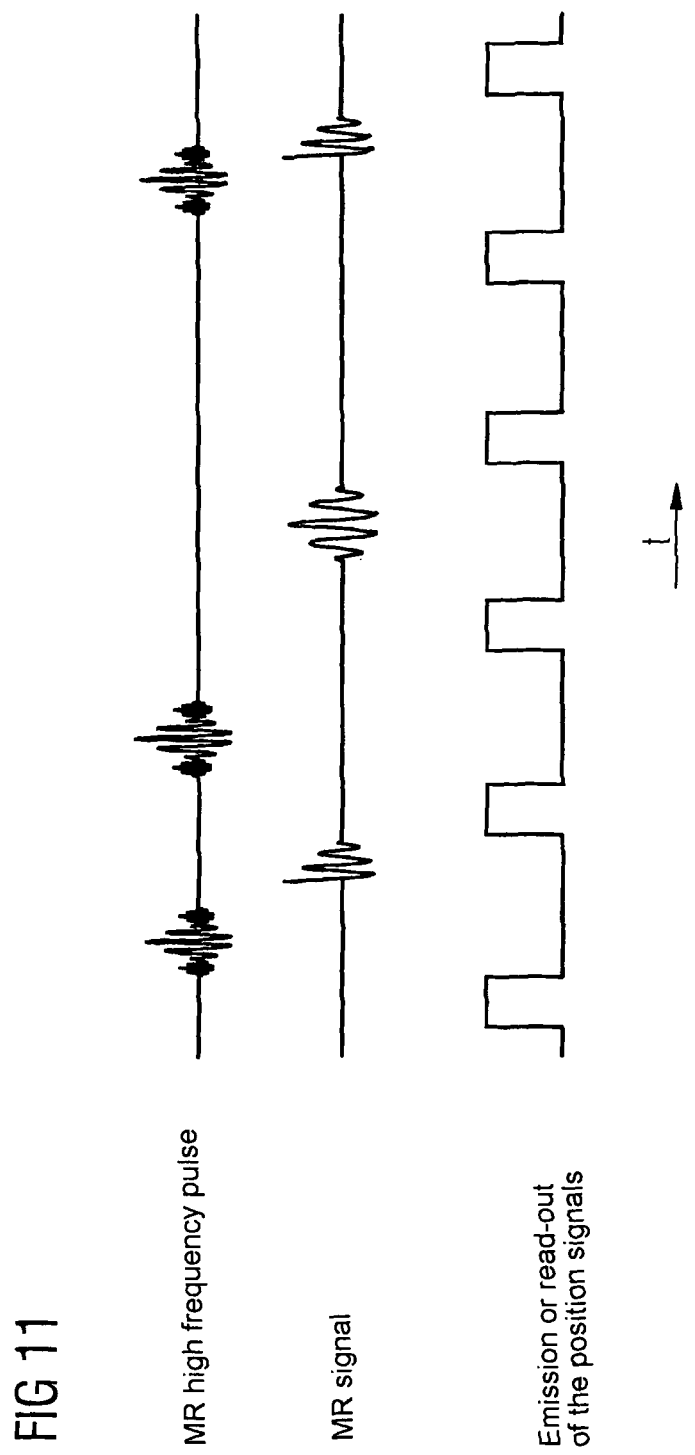

CRYOCATHETER FOR INTRODUCTION INTO A BODY VESSEL TOGETHER WITH MEDICAL INVESTIGATION AND TREATMENT EQUIPMENT

CROSS REFERENCE TO RELATED APPLICATIONS

This application claims priority of German application No. 10 2005 050 344.6 filed Oct. 20, 2005, which is incorporated by reference herein in its entirety.

FIELD OF THE INVENTION

The invention relates to a cryocatheter for introduction into a body vessel or into an organ, with a catheter inner which is surrounded by a catheter sheath, and with a catheter tip arranged at its distal end, with a feed line for an expansion and cooling agent arranged in the catheter sheath or the catheter inner and with a balloon, arranged close to the catheter tip, which can be expanded and contracted again by means of the expansion and cooling agent. It further relates to a medical investigation and treatment device with a cryocatheter of this type.

BACKGROUND OF THE INVENTION

Among the most frequent diseases with fatal consequences are diseases of the vascular vessels, in particular heart infarcts. This is caused by diseases of the coronary vessels, so-called arteriosclerosis. With this, the diameter of the vessels is reduced by deposits (arteriosclerotic plaque) on the vessel walls to the point where an individual coronary blood vessel, or several, may be blocked. It has now been recognized that the danger of suffering a coronary infarct does not depend primarily on the reduction in the diameter of the vessels. Rather, it depends on whether the thin protective layer, which covers the arteriosclerotic deposits, remains intact. If this ruptures, blood platelets preferentially deposit at the breakage site, and within a short time these completely close up the blood vessel and thus cause a coronary infarct.

A narrowing, also referred to as stenosis, of the coronary vessels, as a possible precursor of a blockage which may lead to a coronary infarct, may be diagnosed for example in the course of coronary angiography. During the latter it is normal to introduce into the coronary vessels a catheter, through which an X-ray contrast agent is injected into the region of the vessels to be investigated. An X-ray photograph of the region of the vessels is then prepared, and the catheter is removed again. The inner space within the blood vessels, which is filled with the contrast agent, then shows up on the X-ray image. The resulting image is also referred to as an angiogram. One disadvantage of this method consists in the fact that it only shows the diameter of the vessels which is usable by the blood flow, or the point of narrowing, as a silhouette. It is not possible to make any statement about the deposits, in particular their thickness or the degree of the inflammatory process.

Recently is has also become possible, for the purpose of more precisely diagnosing a stenosis, to introduce into the coronary vessels a so-called ultrasonic catheter with an imaging intravascular ultrasonic sensor (IVUS sensor). An ultrasonic catheter of this type is, for example, known from DE 198 27 460 A1. The IVUS sensor supplies ultrasonic images from the interior of the vessel, whereby the image formed is normally a 360° sectional view of the vessel wall and also the underlying tissue layers.

Alternatively, the investigatory catheter can also be equipped with a sensor for optical coherence tomography (OCT) or with a sensor for intravascular magnetic resonance tomography (IVMRI=intravascular magnetic resonance imaging).

Optical coherence tomography imaging supplies high-resolution images which, in particular, show the structures in the region of the surface of the vessel comparatively exactly. The principle underlying this method is that the catheter radiates light fed via an optical guide, preferably infrared light, into the vessel, with the light reflected by the latter being coupled back into the optical waveguide and fed to an analysis device. In the analysis unit, the coherence of the reflected light is analyzed against the reference light—in a way similar to that in a Michelson interferometer—to generate an image. An OCT investigatory catheter is known, for example, from U.S. Pat. No. 5,921,926. With the OCT method, the section of the vessel to be investigated must be briefly cleared of blood. For this purpose, the blood flow is normally interrupted during the image capture by a closure plug, and the section of the vessel washed out using a physiological saline solution.

Another imaging method, which is known in particular for its good representation of soft tissues, is magnetic (core) resonance tomography. With this method, the magnetic moments (core spins) of the nuclei of atoms in the tissue to be investigated are aligned in an external magnetic field and excited by irradiated radio waves into a gyroscopic movement (precession), whereby relaxation processes induce in an associated receiving coil an electrical magneto-resonance signal which forms the basis for calculating an image. There has recently been success in miniaturizing the elements which generate the magnetic field, and integrating them into an imaging IVMRI sensor in an investigatory catheter, in a way which enables the intracorporal or intravascular use, as applicable, of the MRI method, whereby the necessary static magnetic field is also generated or applied, as appropriate, within the patient's body. A solution of this type is described, for example, in U.S. Pat. No. 6,704,594 B1.

If, using the investigatory methods outlined above, stenoses of the coronary vessels are recognized which are a threat to the patient or greatly limit their capabilities, further treatment steps are generally necessary. Depending on the case, this will involve carrying out either a bypass operation or a balloon dilatation, also known as a "percutaneous transluminal coronary angioplasty (PTCA)". Nowadays, it is preferable to use the PTCA method. With this, the narrowings of the coronary vessels are dilated using a so-called balloon catheter, which is introduced under X-ray control into the region to be treated. In the region of its front tip (at the distal end) this catheter has a balloon which can be expanded, generally using a saline solution under pressure, which is expanded or inflated at the site of the stenosis. So that the enlargement of the vessel does not revert to its original state (restenose), a so-called stent is frequently introduced into the widened section of the blood vessel after the dilation. This stent is a cylindrical mesh, generally metallic, which is plastically reshaped using the balloon, and lies against the inner wall of the vessel when it is expanded.

Even after the implantation of a stent, restenoses can occur. Reasons for postinterventional restenosis are the continuation of the causative arteriosclerosis, and the response of the vessel wall to the PTCA-induced trauma. For this reason, techniques are now available to treat the section concerned of the vessel prior to the implantation of a stent, and thus prevent restenosis. For example, clinical studies have shown that endovascular irradiation of the vessel wall with beta and/or gamma radiation (brachytherapy) reduces restenoses. The mechanisms are not yet fully clarified, but various models are being discussed, e.g. cell death, cell inactivation, inhibition of cell migration, suppression of the vascular structural remodeling, and blocking of the extracellular matrix synthesis. The disadvantage of brachytherapy lies in the additional radiation load on the patient and in the expensive logistic process which the radioactive sources necessitate in the clinic (procurement, storage, disposal).

A new method is currently in clinical research: pretreatment of the stenosis before or during dilatation, with the help of cryotechnology (cryogenics). In this case, a so-called cryocatheter is fed into the vessel as far as the stenosis. As soon as the stenosis is reached, liquid nitrogen is introduced into the catheter, this reaching the gaseous state by the time it arrives at the catheter tip, and when it expands it blows up a dilation balloon. The nitrogen thus functions as both an expansion medium and a coolant. In other words, the section of the blood vessel which is affected by the stenosis if briefly cooled to a very low temperature and, at the same time, is widened by the stretching of the balloon. The cold-induced "sclerosis" of the tissue achieves a similar effect in the vessel wall as with brachytherapy, i.e. the restenosis rate is significantly reduced, but the patient is exposed to no additional radiation load. This method is described, for example, by James D. Joye et al. in "In Vivo Study of Endovascular Cryotherapy for the Prevention of Restenosis", which can be ordered on the Internet under http://www.cryoinc.com. A cryocatheter which is suitable for carrying out the method is known, for example, from U.S. Pat. No. 6,355,029 B1.

All in all, it is a disadvantage that the known procedure is multiply invasive, i.e. several different catheters must be introduced—for preliminary investigation and for treatment—one after another. However, each invasion has a certain associated risk for the patient. The fact that the investigatory catheter must first be withdrawn again from the patient's vascular system, before the cryocatheter provided for the cryotherapy and widening of the blood vessel can be introduced, means that problem are frequently presented in locating again exactly the treatment region determined during the preliminary investigation. Specifically, when it is being introduced the cryocatheter can only be observed in outline in the angiography X-ray image, making its manipulation more difficult and the position of the catheter tip within the section of the vessel which is to be treated can only be approximately estimated. It is possible that the cryocatheter is not precisely positioned in the target area during its use, thereby increasing the risk of restenosis.

SUMMARY OF THE INVENTION

The objective underlying the invention is thus to specify a cryocatheter of the type cited in the introduction which, by simple manipulation can be positioned precisely at the target point in the bodily vessel, and which minimizes the load on the patient from invasive interventions. In addition, the intention is to specify medical investigation and treatment equipment, incorporating the catheter, which makes available a suitable infrastructure for the use of the catheter.

In relation to the cryocatheter, the said object is achieved in accordance with the invention in that an image capture device, with at least one imaging sensor for mapping the region of the vessel around the balloon, is positioned near to the catheter tip.

The invention is based on the consideration that the number of invasive interventions to which the patient is subjected can be reduced if the diagnosis of a stenosis and any treatment and control measures which may be necessary, in particular cryotherapy and widening of the section concerned of the blood vessel, take place in a common "operation" or therapeutic step. To this end, a cryocatheter which is provided with an expandable balloon and a feed line for an expansion and cooling agent should also have available an integral image capture device for intravascular imaging.

For this purpose, at least one imaging sensor is arranged and constructed close to the catheter tip, preferably in the catheter inner, in such a way that the region of the vessel in which the balloon is positioned can be mapped. With this, even during the operation to introduce the catheter, continuous image capture enables its movement to be continually captured and monitored in the region of the catheter tip. Besides this, there is the possibility of positioning the catheter with the balloon absolutely exactly in the target area, i.e. in the stenosed section of the vessel, since it is exactly the area of the vessel in which the balloon is located which is shown by the image capture device. That is to say, the actual position of the balloon can be captured and the latter can be exactly positioned. Equally, it is possible to carry out continuous checking of the position and orientation during and after the cryotherapy and widening of the vessel, with absolutely no movement or swapping of the catheter. That is to say, for a single invasion a cryocatheter fitted with an imaging sensor permits a precise diagnosis of the stenosis and precisely positioned alignment during simultaneous cryotherapy and dilation of the vessel. The intravascular imaging is more informative and reliable than (external) angiographic X-ray checking. The image capture device integrated into the cryocatheter supplies, on the one hand, high-resolution images, directly from inside the vessel, which can be subject to precise diagnostic analysis and on the other hand the number of invasions and the number of different catheters which must be used is minimized. In the simplest case it is only necessary to use one single catheter, namely the imaging cryocatheter.

For the purpose of making an image of the region of the vessel close to the balloon, it is appropriate if the image capture device is arranged to be essentially directly adjacent to the balloon. In this case it can be arranged so that relative to the catheter tip it is in front of or behind the balloon, or at the same level. In the last case, the balloon should preferably consist of a material which is transparent to the imaging method.

Optionally, a stent which is to be implanted in the body vessel is arranged on the balloon of the cryocatheter, and is widened by the expansion of the balloon and thereby fixed in the section of the vessel which has been pretreated by the cryogenic effect. All the investigatory and treatment measures, including the stent implantation, can then be effected almost simultaneously in one operation, and with the one and same cryocatheter.

It is appropriate if the stent is a metallic stent, e.g. made of stainless steel or Nitinol. As a prophylaxis against restenosis after the PTCA, the stent can also have a suitable coating. This coating can be, for example, a nanocoating and/or a medicamental coating. In the latter case we also speak of a "drug eluding stent". In an alternative variant, the stent can also be manufactured from a bioresorbtive material, such as a biological material, bio-engineering material, from magnesium or from plastic, in particular a polymerous plastic, which breaks up after a prescribed period of time and is excreted or broken down by the blood circulation or the metabolism.

The expansion and cooling agent provided will preferably be nitrogen, which is kept ready in liquid form in a storage container external to the cryocatheter. Nitrogen is comparatively easy to handle and to cool down to the required temperatures. In addition, in the highly unlikely event of a leak in the balloon or within the feed line in the catheter, it does not produce any form of toxic reaction or other disadvantageous effect on the vascular system or the organism. This ensures especially high levels of safety for the patient.

Apart from the feed line for the expansion and cooling agent, a separate bleed line is usually introduced additionally into the catheter sheath or the catheter inner, with an adjustable discharge valve by which it can be closed off, for "bleeding" the expanded balloon, i.e. for a controlled discharge of the expansion and cooling agent which has flowed into the balloon. By regulation of the mass in- and out-flows, which are independent of each other, and the temperature of the expansion and cooling agent on entry, it is possible to control the pressure behavior in the balloon largely independently of the temperature behavior, and to hold them constant or selectively influence them over a longer treatment time, e.g. 1-2 minutes.

It is advantageous if the image capture device incorporates at least an IVMRI sensor for intravascular magnetic resonance tomography and/or an IVUS sensor for intravascular ultrasonic imaging and/or an OCT sensor for optical coherence tomography. For each of these three types of sensor, the underlying imaging method is capable of supplying, over and above the visual information available from coronary angiography, additional medical information about the arteriosclerotic deposits, such as their thickness and any inflammatory processes. Apart from simplified manipulation and navigation of the cryocatheter, the image capture device thus also gives increased diagnostic benefits. If a stent is to be implanted using the cryocatheter, then with the help of the image capture device it is also possible to check its position and seating in the vessel so that, if necessary, it is possible to undertake appropriate corrective measures, still as part of the original intervention.

Optical coherence tomography has the particular advantage that structures in the neighborhood of the vessel surface can be shown with a very high resolution of detail; in some cases, it is possible to show microscopic tissue views. On the other hand, intravascular ultrasonic imaging is especially suitable for a good resolution of deeper-lying tissue layers. Alternatively, using intravascular magnetic resonance tomography it is possible to achieve a particularly good and differentiated display of the soft parts around the vessel, which is of advantage when investigating arteriosclerotic plaque. The IVMRI method has in addition the advantage that it is capable of imaging a stent, which is to be implanted in the vessel, with exceptional clarity and high contrast. The applies also, in particular, for new types of bioresorbtive stents, which are transparent and therefore invisible with coronary angiography. With an IMRI sensor integrated into the cryocatheter, but also with an IVUS sensor or an OCT sensor, precisely targeted positioning of a stent, together with subsequent precise checking of its location in the vessel, is therefore possible.

In a first advantageous variant of the cryocatheter, a number of imaging sensors of the same type are provided, these being distributed over the cross-section of the catheter and in each case directed towards the vessel wall. The sensors, pointing outwards in a star formation, for example, and preferably arranged in a common cross-sectional plane, can capture a number of images simultaneously, each with a different viewing angle, which can be combined in an image processor with a data link to the cryocatheter to give a 360° sectional view of the vessel wall and the adjacent tissue layers. In this case, the imaging sensors are in fixed positions relative to the catheter sheath. With this form of embodiment, no rotational drive is required for the catheter or the imaging sensors. Preferably, the imaging sensors will be connected via a multiplexer to a common signal line, running inside the catheter sheath or in the catheter inner, where it is appropriate if the actuation or signal polling of the sensors is carried out cyclically. A small number of signal lines, preferably only a single one, is advantageous for the flexibility and pliability of the catheter.

In an alternative second variant, the image capture device has at least one imaging sensor which can be rotated via a drive shaft which leads along the catheter sheath or the catheter inner. This enables a single sensor, generally a directionally sensitive one, to be used to make a 360° sectional image of the vessel wall and the adjacent tissue sections, without the catheter itself or its sheath, as applicable, having to be moved. Apart from this, the space requirement for the sensor unit is less for this variant than with the first variant, or the imaging sensor does not need to be so greatly miniaturized, which reduces the manufacturing costs.

Furthermore, it may be logical to accommodate several imaging sensors, of different types, in the region of the catheter tip. Especially preferred are the combinations IVUS/IVMRI or IVUS/OCT. The individual sensors of these two combinations each supply image data which is complementary to the other, which enhance each other in a particularly suitable way. For example, the combination IVUS/OCT results in a good resolution in the deeper-lying regions and at the same time a very high resolution in the nearby regions of the vessel wall. The individual images which correspond to one another can be displayed, either separately, together beside each other or even overlaid or merged, on a display monitor of an electronic analysis and display device connected to the catheter. For example, it is possible to generate a combined IVUS/OCT image which is made up of an essentially circular-shaped inner section of image from an OCT image (the nearby region) and an outer IVUS image section which surrounds the circular-shaped inner area (more distant region with deeper-lying tissue layers). The corresponding applies also for the IVUS/IVMRI combination, where the IVMRI sensor covers the nearby region directly adjacent to the vessel wall, in which any stent may also be located.

It is also possible to integrate all three types of imaging sensors into the cryocatheter, with the sensors being driven by a common drive shaft if necessary.

In order to achieve the simplest possible construction with such a combination of imaging sensors, provision can be made that the sensor for the intravascular ultrasonic image capture system and the sensor for the optical coherence tomography (and/or the magnetic resonance sensor) can be driven by a common drive shaft. This renders superfluous a separate drive shaft or other type of drive for the second sensor. In the case of the OCT sensor it is moreover appropriate if the optical fiber used for transmitting the light is also the drive shaft. In this case, the optical fiber serves on the one hand to guide a light beam, which is shone into the area under investigation, and at the same time the reflected light is fed back via the optical fiber, and the optical fiber serves as the drive shaft for the OCT sensor, if applicable for both sensors. In accordance with an advantageous development, provision can also be made that the two sensors arranged in the catheter tip can be driven, via a common drive shaft and an intermediate microgearbox, at different rotational speeds which are appropriately adjusted for the imaging method concerned.

It is advantageous if the catheter sheath of the cryocatheter has at least one window, which is transparent to the underlying imaging method, in the region of the imaging sensor concerned. Depending on the sensor type, this will be an optically transparent window (OCT), an acoustically transparent window (ultrasound) or a window which is transparent to the IVMRI radio waves, which will preferably extend around the entire perimeter of the catheter sheath.

For the purpose of improving the imaging, it is advantageous to provide, in the catheter sheath or the catheter inner, at least one contrast agent feed line for a contrast agent, which opens out at an outlet arranged on the outer side of the catheter sheath close to the imaging sensor. This can be used, in the case of MRI imaging, to introduce an MRI contrast agent, for example a contrast agent based on gadolinium, through the feed line or the duct in the catheter directly into the vessel of interest or the body cavity, as applicable. Compared to its insertion via a peripheral vein this has the advantage that the contrast agent becomes effective with no time delay. Correspondingly for ultrasonic imaging, a contrast agent based on sulfur hexafluoride can be injected. Ultrasonic contrast agents of this type form temporary gas bubbles in the blood stream, and thereby change the reflection characteristics in the section of the vessel concerned, which results in an improvement in the image quality if the ultrasonic signal analysis unit is appropriately adapted. Ultrasonic contrast agents have been used until now mainly with extracorporeal sound sources.

In an advantageous development at least one contrast agent feed line is provided in the catheter sheath or the catheter inner, for an X-ray contrast agent, which opens out at an outlet arranged on the outer side of the catheter sheath. With this, it is also possible to effect a particularly good mapping of the region of the vessel which is to be investigated, and treated if appropriate, during coronary angiography, with the image data acquired in this way being a logical supplement to the image data from the internal imaging sensors. Apart from providing a number of feed lines for various purposes, it is also possible that only one single contrast agent feed line is provided, through which various types of contrast agent can be injected in succession into the vessel to be investigated.

For the purpose of improving the visibility of the catheter when illuminated by X-rays, in particular the catheter tip, it is advantageous to provide a number of X-ray opaque marks (X-ray markers), at least in the region of the catheter tip.

In an advantageous development, a number of position sensors or detectors are arranged in the region of the catheter tip, by means of which the current position of the catheter tip, and preferably also its orientation, can be determined. Preferably there will be several electromagnetic transmission coils, in particular three, which work in conjunction with a number of receiving coils or signal detectors arranged externally, i.e. outside the patient. For precise determination of the location in the space, and determination of the orientation and angular relationships, the transmission coils will preferably be arranged orthogonally to each other, whereby it is appropriate to assign to each transmitter its own receiver. In an alternative form of embodiment, the roles of the transmission and receiving units can also be interchanged, i.e. the receiving coils are fixed to the catheter while the transmission coils are preferably arranged statically in space. Alternatively or additionally to the electromagnetic position sensors, use can also be made of ultrasonic position sensors and receivers. In a further advantageous form of embodiment, alternatively or additionally to the position sensors hitherto described the imaging IVMRI sensor and/or the IVUS sensor can also act as a position transmitter, and can provide a position signal for a receiving unit arranged in the space. On the one hand, the position details thus obtained simplify the safe introduction of the catheter and its navigation to the target area, and on the other hand they provide advantageous support for the construction of three-dimensional images, which has yet to be described, from a number of two-dimensional cross-sectional images.

In a further advantageous form of embodiment, at least one magnetic element can be provided in the region of the catheter tip, for guiding the catheter by means of an external magnetic field. With this so-called magnetic navigation, the catheter is then controlled and driven by an external magnetic field. The magnetic element concerned can be a permanent magnet or an electromagnet. In particular, provision can also be made to use a wire-wound coil, with appropriate sizing and actuation, optionally as either a receiving coil or receiving antenna for positioning signals from an assigned positioning signal transmitter, or as electro-magnet for guiding the catheter magnetically. For the purpose if increasing the permeability, and thus also raising the achievable magnetic field strengths, the coil can in this case be equipped with an iron or ferrite core, or similar.

As an alternative to the guidance of the catheter by an external magnetic field, a mechanical form of navigation can be provided. For this purpose the catheter has integrated into it suitable mechanical elements, e.g. in the form of pull wires and the like, which permit a temporary mechanical deformation, stretching and/or bending of the catheter or individual selectable sections of the catheter, in particular the catheter tip, by external pulling and pushing forces. Preferably, the mechanical and/or magnetic guidance of the catheter is effected automatically with the help of a computer-aided control device.

In a particularly preferred form of embodiment, the electrical functional units which incorporate the imaging sensors and, if applicable, a number of position sensors together, if applicable, with further sensors, are arranged on or in an inner body which can be pushed into a corresponding cavity in an outer body which incorporates the catheter sheath, the balloon and, if applicable, the stent. In this case it is appropriate if the supply and signal lines provided for linking the electrical functional units with an analysis and control unit, and/or the drive shaft provided for rotating the imaging sensors, are arranged on or in the inner body, while a feed line for expansion and cooling agent and/or a discharge line for an expansion and cooling agent used for the purpose of cryotherapy and the expansion of the balloon, and/or at least one contrast agent feed line, are preferably arranged on or in the outer body. With this design, the components concerned are easily exchangeable if needed, such as for maintenance or cleaning, and in their disassembled state are also particularly easy to access. This also makes it possible to introduce into the coronary vessels an "outer" cryocatheter which is appropriate for the applicable anatomical conditions and the site and purpose of use and, during the investigation and treatment, to exchange the "inner" catheter or the inner body which has the imaging and other electrical functional units, as applicable. For example, if it is advantageous or logical for diagnostic purposes it is then possible to replace an IVMRI inner catheter by an OCT inner catheter, without subjecting the patient to another invasion, that is to say by any swapping or movement or other manipulation of the outer catheter. Nor is an initial demanding navigation of the replacement inner catheter to the target region necessary, nor its readjustment at that site. Rather, it is sufficient to push it up to a positional stop in the cavity in the outer catheter, which during the procedure remains in the position it had previously reached or adopted in the vessel.

It is advantageous if each of the supply and signaling lines provided for linking the electrical functional units to the analysis and control unit has a protective layer for the purpose of (electro-)magnetic screening. The electronic circuits and other components integrated into the functional units or into the sensors can also be (electro-) magnetically screened in this way. The same applies for other physiological sensors integrated into the cryocatheter. These could be, in particular, temperature and pressure sensors for the purpose of monitoring the vessel temperature and the pressure in the vessel. This ensures that signal transmission and processing is undistorted even in spite of the comparatively strong magnetic fields involved, for example, in MRI imaging or with external magnetic guidance fields. The protective layer for magnetic screening can be, for example as described in U.S. Pat. No. 6,506,972 B1, a thin-film layer of conductive nanoparticles, on a basis such as silicon dioxide, aluminium oxide, silicon nitrate or carbon.

It is advantageous if the electrical functional units of the cryocatheter, in particular the imaging sensors and the position sensors, are protected against the effects of the cooling agent by a thermal insulation or sheath, so that their functional capabilities are not degraded as a result of excessively low temperatures.

During the cryotherapy, it is advantageous if the temperature and pressure of the expansion and cooling agent in the balloon are each monitored by a sensor. The temperature sensor can, for example, be in the form of a thermocouple. The in- and out-flow of the expansion and cooling agent may possibly be readjusted by reference to the temperature and pressure data.

The connections for the imaging and physiological sensors, together with those for the position sensors, are decoupled by an associated galvanic isolator from the comparatively high mains supply voltage, typically 110 V or 230 V, in order to exclude any possible danger to the patient from it. Here, optical decoupling is particularly advantageous.

It is advantageous for the cryocatheter to have on its outside a coating which reduces the frictional resistance when it is guided or slid through the vessels. It is appropriate if this coating is hydrophilic in character. It could be, for example, a silicon coating or a nanocoating based on nanotechnology. The coating is further chosen so that it counteracts or prevents possible thromboses, where the concepts and measures for this are familiar to the specialists.

Preferably, the cryocatheter will be provided with a microchip or tag called an RFID transponder, in which the technical data for the catheter and/or documentation of the history of the catheter's usage can be stored, and can be read out and manipulated by a non-contact method using an external transmit and receive unit, also called an RFID reader, (RFID =Radio Frequency Identification). The RFID transponder and the associated RFID reader are components of a DP-supported RFID infrastructure which contributes to the better tracking of the catheter in the logistic chain in a hospital or other medical treatment facility. The items of technical data stored in the RFID tag can also be called on in making device-specific presettings or modifications, automatically and reliably, for an analysis and control unit which is to be connected to the cryocatheter.

It is appropriate to integrate the cryocatheter into a medical investigation and treatment facility, where the cryocatheter's imaging sensor has a data link to an analysis and control unit. Here, the analysis and control unit incorporates an electronic image processing unit for the visual processing of the sensor signals and a display unit for displaying the images calculated from the sensor signals. The position sensors or detectors arranged in the catheter inner and/or the receive and transmit units, which are assigned to these position sensors and are arranged outside the patient, are also linked to the analysis and control unit, to which they communicate a position signal from which it is possible to determine the current position of the catheter tip and, preferably, also its spatial orientation. It is advantageous if the position data determined is further processed in a 3D correction module in the image processing unit, and used for the generation of a reduced-artifact three-dimensional solid dataset from a number of two-dimensional sectional images.

It is advantageous to obtain the two-dimensional sectional images, on which the generation of the three-dimensional images is based, by moving the rotating imaging sensor forward or backward in the vessel. In the latter case, the use of which is preferable, the method is also known as the "pull-back method". For an advance or retraction of the cryocatheter which can be especially well controlled, with a defined and preferably constant velocity, the medical investigation and treatment equipment can also incorporate an appropriate drive device for the catheter, which it is appropriate to actuate via the analysis and control unit.

Since the cryocatheter generally has a smaller cross-section than the vessel to be investigated, and can therefore move to and fro within the diameter of the vessel, movement artifacts can arise during the 3D image processing. By involving the position data, artifacts of this type can be significantly reduced or even completely avoided. In this way, it is possible to generate more realistic and more informative 3D recordings of the region under investigation, which permit improved medical diagnosis.

It is appropriate if the artifact correction, implemented by hardware or software in the 3D correction module, first determines from the 2D sectional images the center line of the vessel, and thereby also advantageously the approximate envelope of the vessel. This can be done, for example, by interpolation between the boundary points determined during the forward or backward movement of the catheter, during which the catheter tip contacts the vessel wall or bumps into it. By reference to the geometric data so obtained, which furthermore also includes the minimum and maximum diameters of the vessel, it is then possible to effect an offset correction, i.e. a displacement of individual images in the plane of the image and also, if appropriate, a rotation of individual 2D images, before they are "assembled together" to form the desired offset- and artifact-corrected 3D image.

In a further advantageous embodiment, any movements of the patient, including in particular movements of the organs together with movements of the thorax and the blood vessels due to breathing and beating of the heart, are detected and taken into account (so-called gating) in correcting for artifacts and in producing the 3D reconstruction. To this end it is advantageous if the analysis and control unit, or their 3D correction module, as applicable, is linked on the data input side to a movement sensor which can be attached to the patient and/or to a number of physiological sensors. The principle on which the movement sensor works can be electrical, capacitive, magnetic, acoustic or even optical, and in a particularly advantageous variant it can be constructed using wireless RFID transponder technology. The movement sensor can be held rather like a plaster, with an adhesive surface and an integral sensing chip, which is stuck onto the patient during the investigation and disposed of after use. In addition or alternatively, a purely mathematical/statistical movement correction and image postprocessing can be effected in the analysis unit with the help of known correction algorithms.

Further physiological sensors can record measurement data, in particular on breathing or vessel pulsation, or can also record an electrocardiogram (ECG), and feed these to the 3D correction module for the purpose of eliminating movement artifacts. For example, for the purpose of eliminating the breathing artifacts use can be made of a chest band which determines the amplitude and frequency of breathing through appropriate sensors. Alternatively, the amplitude and frequency can be calculated from the envelope of the ECG signal and fed to the correction unit of the image processing unit. In addition, the pulsing of the vessels can be determined by analyzing the ECG or the blood pressure curve. In the case that the cryocatheter incorporates several imaging sensors of different types, e.g. an IVUS sensor in combination with an OCT sensor, the analysis and control unit will preferably have an image merging unit which enables the various types of images to be registered (aligned with the correct position and phase) and merged so that merged images, which are especially informative, can be shown on the display unit.

The advantages which the invention realizes consist in particular in the fact that the integration of an image capture device into a cryocatheter achieves a reduction in the invasive procedural steps required for the investigation and treatment of coronary vessel diseases. The images from the imaging sensor supply important additional medical information about the arteriosclerotic deposits, e.g. about inflammatory processes, which can be taken into account in deciding on any further treatment steps. The manipulation and navigation of the cryocatheter into the target region is significantly simplified due to the integrated imaging. It is therefore possible in some circumstances to forgo angiographic X-ray control with the associated radiation load. In addition, it is significantly simpler and more accurate to check the correct positioning of an implanted stent by referring to the intravascular images than has been possible until now. This applies in particular for bioresorbtive stents, which are practically impossible to see when using conventional coronary angiography. The cryogenic procedure before the stent is inserted reduces the risk of a restenosis, with no additional radiation load arising, in contrast to brachytherapy.

The concept proposed here is not restricted to the coronary vessels, but can be used for all the cavities, vessels and organs in a human or animal body.

BRIEF DESCRIPTION OF THE DRAWINGS

Various exemplary embodiments of the invention will be explained in more detail by reference to a drawing. This shows.

DETAILED DESCRIPTION OF THE INVENTION

Figure 1:
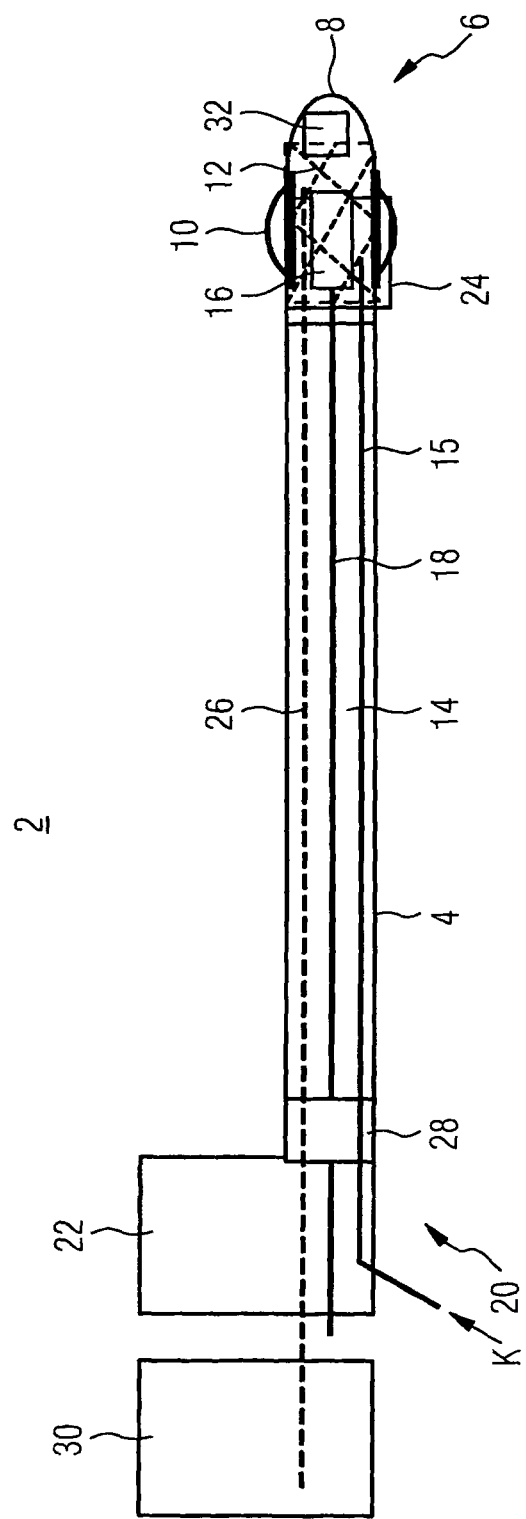
FIG. 1 a schematic longitudinal section through a cryocatheter with an integral imaging sensor in accordance with a first form of embodiment, FIG. 2 a schematic longitudinal section through a cryocatheter with an integral imaging sensor in accordance with a second form of embodiment, where the cryocatheter incorporates an exchangeable inner catheter which can be pushed into an external catheter, FIG. 3 a longitudinal section through a cryocatheter, similar to that in FIG. 1 but with two imaging sensors of different types arranged one behind the other, FIG. 4 a longitudinal section through a cryocatheter, similar to that in FIG. 2 but with two imaging sensors of different types arranged one behind the other, FIG. 5 a schematic diagram of medical investigation and treatment equipment incorporating a cryocatheter with an integral imaging sensor, FIG. 6 a schematic diagram of further operational devices associated with medical investigation and treatment equipment, FIG. 7 an IVMRI sectional image, captured by an imaging IVMRI sensor, of the region of a vessel under investigation and a schematic representation of a three-dimensional solid dataset constructed from a number of IVMRI sectional images, FIG. 8 an IVUS sectional image and a solid dataset derived from it, FIG. 9 an OCT sectional image and a solid dataset derived from it, FIG. 10 a combined IVUS/OCT sectional image and a solid dataset derived from it, and FIG. 11 a schematic sketch illustrating the time-displaced, pulsed communication of detector signals.

The cryocatheter 2 shown in FIG. 1 has an outer catheter sheath 4 and a rounded catheter tip 8 arranged at its distal end 6. A balloon 10, which can be expanded by an expansion and cooling agent K, is provided near to the catheter tip 8, with a stent 12 arranged on its outside. Liquid nitrogen is kept available in an external storage container as the expansion and cooling agent K, and if required is pumped at a pressure of 8-15 bar into the balloon, through a feed line 15 which runs through the catheter inner 14 of the catheter. By expansion of the balloon 10 it is possible to widen a stenosed coronary vessel as part of a PTCA treatment. At the same time, the vessel wall in the region of the balloon 10 is greatly cooled by the nitrogen which evaporates while still within the feed line 15 or when it enters the balloon 10. Depending on the duration of the cryogenic procedure, temperatures of between −10° C. and −80° C. in the interior of the balloon are advantageous. A recurrence of the vessel stenosis (restenosis) is thereby prevented. When the balloon 10 is expanded the stent 12, which is in the form of a metallic wire mesh, is stretched beyond its elastic limits so that subsequently to the balloon stretching it retains its shape. The stent 12, which was originally fixed to the balloon 10, then separates from the balloon 10 and remains in the widened coronary vessel as a support to the vessel even after removal of the cryocatheter 2. Before drawing the cryocatheter 2 out from the vessel, the expansion and cooling agent K in the balloon 10 is completely drained. For this purpose, an outlet duct (not shown here) is provided, running in the catheter inner 14. Instead of a single balloon 10, an inner balloon nested within an outer balloon can also be provided. The stent 12 is optional; depending on the circumstances of the individual case the implantation of a stent may be forgone.

For the purposes of improved diagnosis of vessel diseases, accurately targeted cryotherapy and widening of the vessel and, where applicable, checking the correct location of a stent which is placed in the vessel, the cryocatheter 2 is equipped with an image capture device which incorporates an imaging sensor 16 for intravascular imaging.

In a first variant, the imaging sensor 16 is a so-called IVMRI sensor for intravascular magnetic resonance tomography. To this end, a permanent magnet or an electromagnet is integrated into the IVMRI sensor for the purpose of generating a static magnetic field, and a coil which works as both a transmission and receiving coil. The magnet creates field gradients of, preferably, 2 T/m up to 150 T/m in the neighborhood of the vessel or organ which is to be investigated. Here, "in the neighborhood" means at a distance of up to 20 mm from the magnet. Through the coil, depending on the strength of the magnetic field, it is possible to tap off radio waves in the frequency range from 2 MHz up to 250 MHz for the purpose of exciting the surrounding body tissue. Higher static magnetic field strengths call for higher frequencies in the excitation field. The coil also serves to receive the associated "response" of the bodily tissue. Alternatively, separate transmission and receiving coils can be provided.

In contrast to the conventional MRI systems, the IVMRI sensor and the electronic circuits provided for the purpose of signal processing and analysis are laid out in such a way that they work even if the magnetic field is comparatively inhomogeneous with high local field gradients, and can generate appropriate magnetic resonance images. Under these conditions the echo signals which are received are affected in a characteristic way by the microscopic diffusion of water molecules in the tissue under investigation, thus generally permitting an excellent representation and differentiation between different soft parts, e.g. between lipid layers and fibrous tissue. As an alternative to the concept described here, the static magnetic field can also be produced by external magnets. Unlike conventional MRI, even with this form of embodiment the dynamic fields, i.e. the radio waves, are however produced intravascularly, i.e. by transmission and receiving units arranged on the cryocatheter 2.

In a second variant, the imaging sensor 16 is a so-called IVUS sensor for intravascular ultrasonic imaging. The IVUS sensor has appropriate ultrasonic transducers for the emission of primary ultrasonic waves and the reception of reflected ones, such as in the form of piezo-electric elements. Intravascular ultrasonic imaging is particularly suitable for the mapping of deeper-lying tissue layers and vessel structures.

Finally, in a third variant, the imaging sensor 16 can be a so-called OCT sensor for optical coherence tomography. With optical coherence tomography surface structures on the vessel wall can be shown in particular detail, at high resolution.

The imaging sensor 16, which is generally directionally sensitive and directed radially outwards, can be rotated via a flexible drive shaft 18 which runs through the catheter inner 14, so that a cross-sectional image of the section of the vessel under investigation covering 360° can be sampled. For the purpose of rotating the drive shaft 18 and the imaging sensor 16, a rotational drive 22 is provided at the free end 20 of the cryocatheter 2, closed off from the patients body. Around the imaging sensor 16, the catheter sheath 4 has a window 24 which is transparent for the imaging method. The materials of the balloon 10 and the stent 12 are chosen, in the case of IVMRI or IVUS imaging, such that they produce no noticeable weakening or screening of the MRI radio signals or the ultrasonic waves. In the case of OCT imaging, the OCT sensor is arranged relative to the balloon 10 in such a way that the light waves can be tapped off and injected without distortion.

The signals supplied by the imaging sensor 16 (electrical signals or light signals) are conducted via a signal line 26, which also runs in the catheter inner 14, to a connection adapter 28, at the end 20 of the catheter 2 which is closed off from the patient's body, and from there via a signal interface 30 which is shown schematically to an analysis and control unit which is described below. The voltage supply for the imaging sensor 16 can be effected via supply lines, not shown in detail here, which run in parallel with the signal line(s) 26. The signal and supply lines 26 can also be integrated into the drive shaft 18. In the case of OCT imaging, the signal line 26 which runs in the catheter inner 14 can take the form of a light guide (glass fiber). The light guide can also be integrated into the drive shaft 18. The electrical signal and supply lines 26 have in addition a nanocoating to screen them from external magnetic fields and for protection against electromagnetic interference.

Furthermore, in the region of the catheter tip 8 are attached several electromagnetic position sensors 32. For each direction in a three-dimensional coordinate system one transmission coil is provided, this communicating a corresponding position signal to a detector or signal receiver which is assigned to it and is arranged outside the catheter and outside the body of the patient under investigation. Using the position signals, recorded by the detectors and processed in the downstream analysis and control unit, it is possible to determine the current position and alignment of the catheter tip 8 in space.

Arranged in the catheter inner 14 are two contrast agent feed lines, not shown in FIG. 1, each of which opens out at an outlet close to the catheter tip 8 or the imaging sensor 16: one of these feed lines is used, depending on the sensor type, to feed an MRI contrast agent or an ultrasound contrast agent into the region of the investigation and treatment, while an X-ray contrast agent can be injected via the other feed line, for coronary angiography. The final item which is also provided on the catheter tip 8 is a magnetic element, in the form of an electromagnet, which can be actuated via an external analysis and control unit, which if necessary interacts with a magnetic guidance field which can be applied externally, thereby allowing the catheter tip 8 to be navigated and guided magnetically. Provision can be made for the position sensors 32, arranged in the catheter tip 8, also to be used as electromagnets for magnetic guidance. In this case, the position sensors 32 exercise a dual function, whereby it is possible to switch between the one function and the other by means of the analysis and control unit.

Figure 2:
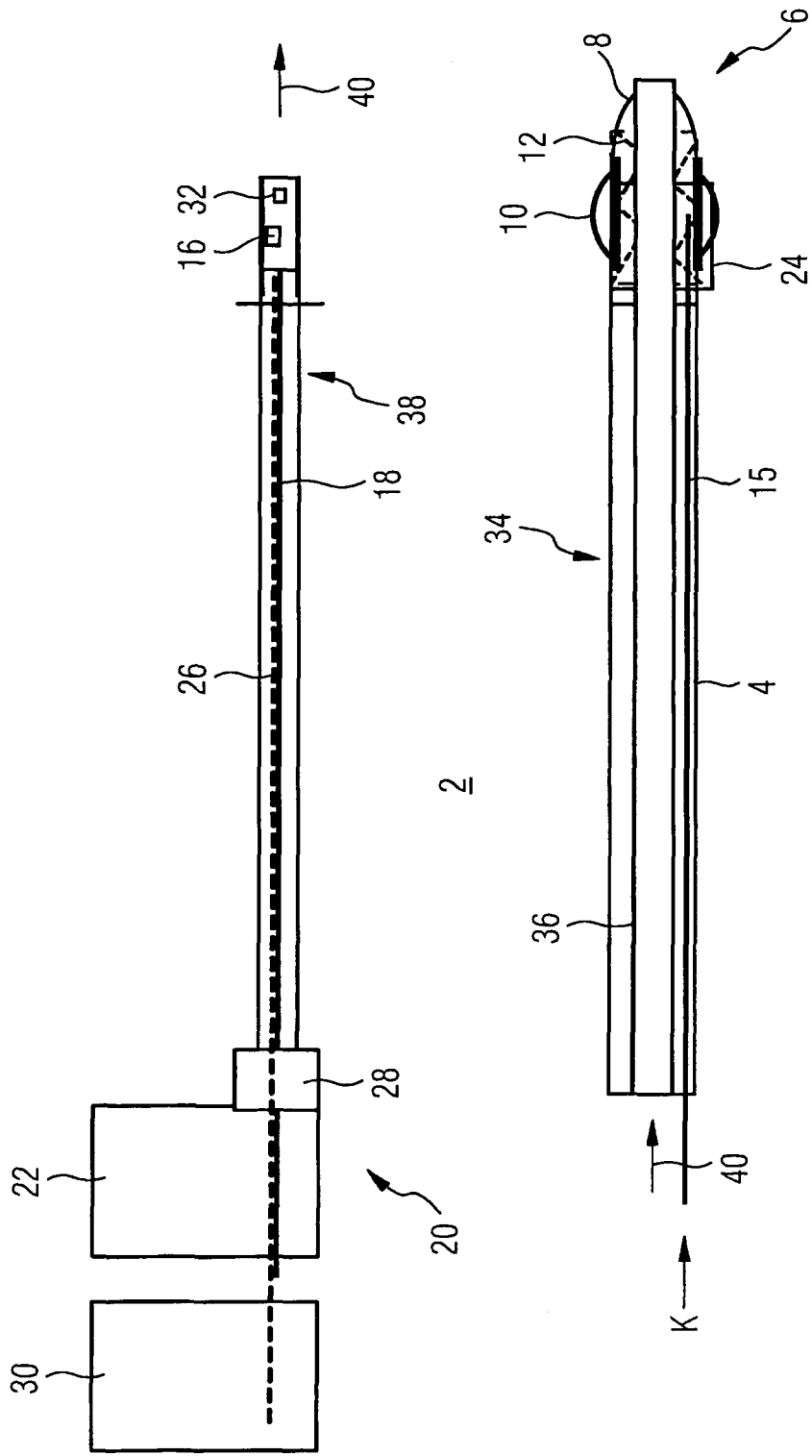

The cryocatheter shown in FIG. 2 has similar functional units to the catheter described for FIG. 1. However, in the case of the form of embodiment shown in FIG. 2 the electrical functional units, including in particular the imaging sensor 16 and the position sensors 32, have been consistently separated from the other functional units, which have a mainly mechanical function. The cryocatheter 2 is thus made up of two main components: first, an outer body 34 or outer catheter which incorporates the outer catheter sheath 4, the balloon 10, the stent 12 plus the expansion agent feed line 15 and the contrast agent feed lines, and secondly an inner body 38 or inner catheter which can be pushed into a corresponding cavity 36 in the outer body 34. On or in the inner body 38 are arranged not only the imaging sensor 16 and the electromagnetic position sensors 32 but also the associated signal and supply lines 26 together with the drive shaft 18 for the imaging sensor 16. For cleaning and maintenance purposes, the two main components of the cryocatheter 2, the inner body 38 and the outer body 34, can easily be taken apart, as shown in FIG. 2. For the purpose of operating the cryocatheter 2, the inner body 38 is simply pushed into the cavity 36 in the outer body 34, as indicated in FIG. 2 by the two directional arrows 40. This can be effected before or even after the introduction of the outer catheter 34 into a coronary vessel which is under investigation in a person. It is therefore even possible to put together a combination of several different inner and outer catheters, which are different but commensurable, which is particularly suitable for the purpose for which it is being used.

Figure 3:
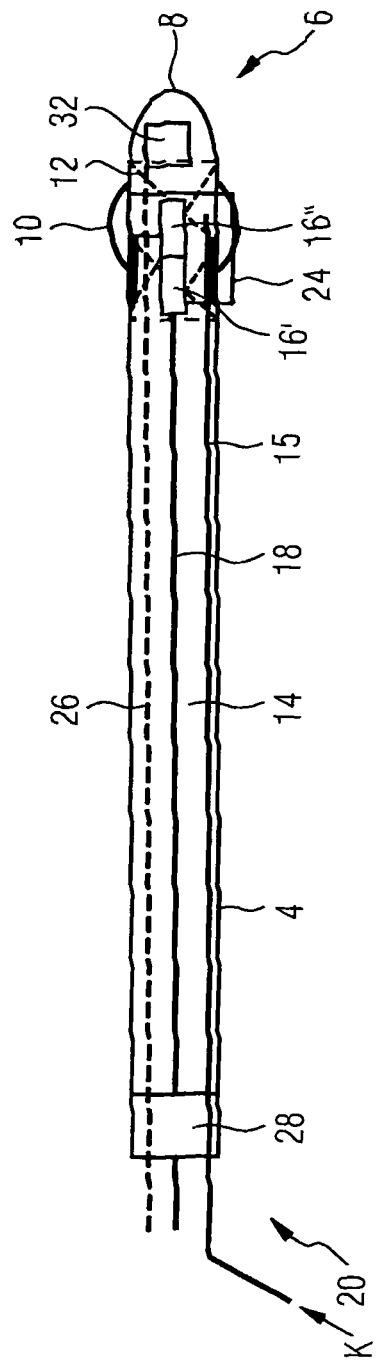

FIG. 3 shows a further preferred form of embodiment of the cryocatheter 2, in which two different imaging sensors 16' and 16", which can be rotated by a common drive shaft 18, are arranged in the region of the catheter tip 8. The sensors 16' and 16", which are arranged one behind the other in a lengthwise direction, could be for example an IVUS sensor and an OCT sensor, where the IVUS sensor could equally well be the front or the rear sensor when looking out from the catheter tip 8. A further preferred combination is made up of an IVUS sensor and an IVMRI sensor. In these cases too, a construction with an inner catheter and a separate outer catheter is possible, see FIG. 4.

Figure 5:
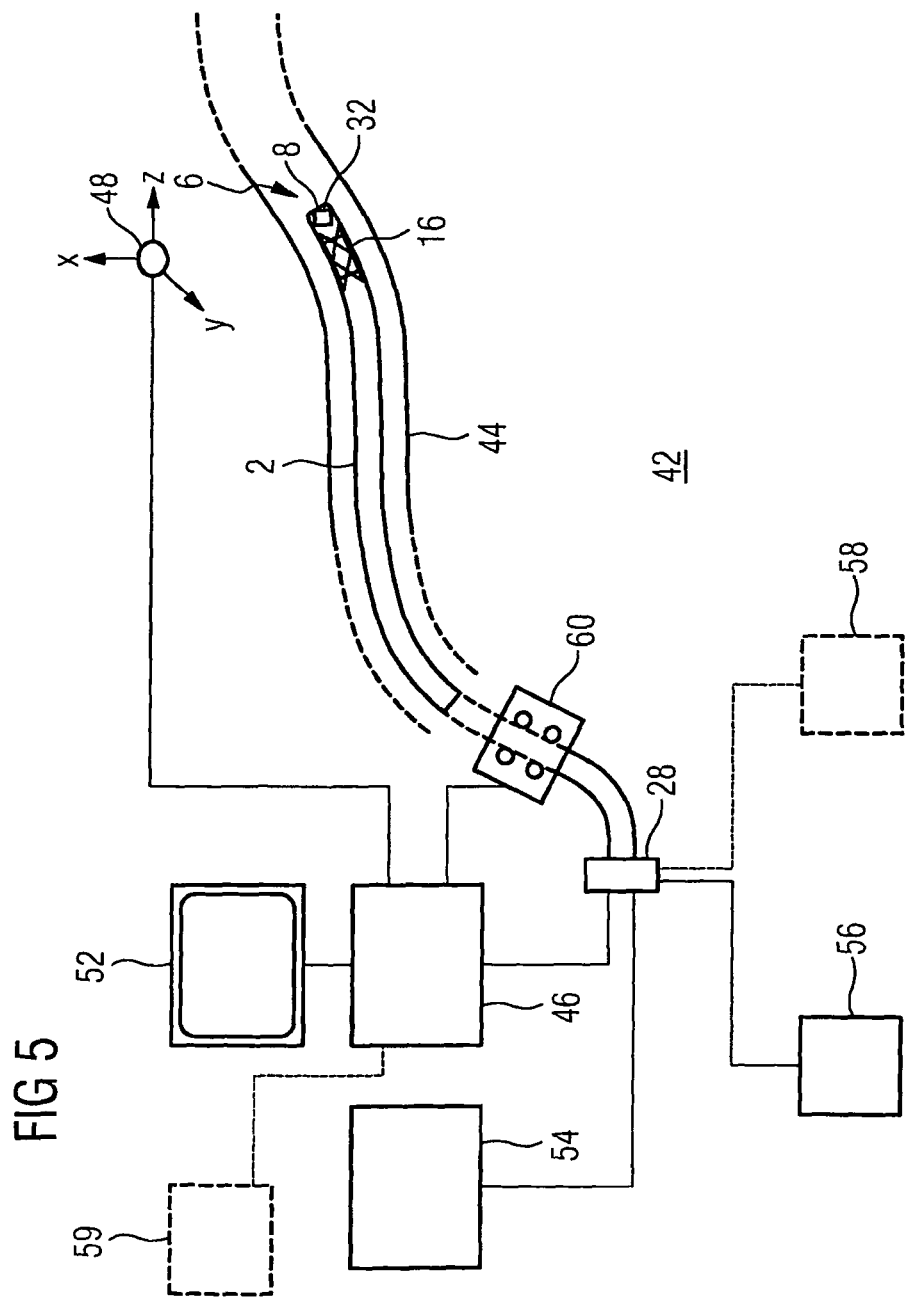

FIG. 5 shows in schematic form some components of medical investigation and treatment equipment 42 which incorporates the cryocatheter 2. The cryocatheter 2 has already been introduced into a body vessel 44 to be investigated. The imaging sensor 16 at the distal end 6 of the cryocatheter 2 is linked on the signal side to an analysis and control unit 46 via a connection adapter 28 arranged at the end 20 which is closed off from the body. The analysis and control unit 46 is also connected, on the signal side, to one or more position signal receivers 48 arranged in the space around the patient, which receive position signals emitted by the position transmitters 32 arranged on the catheter. This permits the position of the catheter tip 8 within a fixed three-dimensional system of coordinates, to be calculated in the analysis and control unit 46.

In the analysis unit 46, cross-sectional images of the vessel under investigation 44 are generated, and postprocessed if appropriate, from the sensor signals of the imaging sensor 16, in doing which it is also possible to construct reduced-artifact three-dimensional volume datasets by incorporating the position data communicated by the position sensors 32. The images thus generated and the data for the region of the vessel under investigation can be displayed on a display monitor of a display unit 52, and thus support the responsible doctor in the diagnosis and treatment of vessel diseases and in manipulating the cryocatheter 2.

The connection adapter 28 is used to effect not only the electrical link from the signaling elements to the analysis and control unit 46 but also the mechanical linkage of the cryocatheter 2 to further external operating devices. These include, in particular, a pump for the expansion agent, which pumps the expansion and cooling agent K, which is stored and cooled in a storage container 54, into the balloon 10 of the cryocatheter 2, and at least one contrast agent injector 56, where the expansion agent pump and the contrast agent injector 56 can each be controlled or regulated, as applicable, through the central control unit 46. In particular, it is also possible to regulate the mass flow of the cooling and expansion agent K, flowing into and out of the balloon 10, via the expansion agent feed line 15 (see also FIG. 1 to FIG. 4) and valves set into the discharge line. The regulation is effected automatically in the control unit 46, on the basis of data supplied by temperature and pressure sensors in the region of the catheter tip 8 and communicated over the signal lines 26 to the control unit 46. Furthermore, using the control unit 46 it is possible to actuate an optional external electromagnet 58, shown here by dashed lines, for guiding the cryocatheter 2 magnetically, and a drive unit 60 for the automatic and smooth advance or retraction of the cryocatheter 2 within the vessel 44. In the case of OCT imaging, the associated (infrared) light source is generally also arranged outside the cryocatheter 2, with its connection to the light guide which runs in the catheter inner 14 being effected via the connection adapter 28.

Optionally, it is possible to integrate into the investigation and treatment system 42 X-ray equipment 59, shown here by dashed lines, in particular cardiological X-ray equipment, which is actuated and read out through the shared analysis and control unit 46. In doing this, the external X-ray image data and the intravascular image data can be exchanged and, for example, combined by image merging. The merged images, which are particularly informative, can then be displayed on the display monitor of the shared display unit 52. The user interface for operating the complete system is designed for the common operation of the X-ray system 59 and the cryocatheter 2.

In operation, the cryocatheter 2 is now introduced into the vessel 44 under X-ray control. This may be effected with the addition of an X-ray contrast agent. To give improved visibility under X-ray illumination, one or more X-ray opaque markers are provided, above all in the region of the catheter tip 8. Even while it is being introduced, the image capture device integrated into the cryocatheter 2 can be active, and can supply images of the vessel 44. Under some circumstances, it is therefore possible to forgo the X-ray control. When the desired target location has been reached, the stenosis or vessel wall, as applicable, can be observed at a higher resolution with the help of the image capture device. On the one hand this enables information to be obtained about the stenosis, and on the other hand the placing of the balloon 10, and any stent 12, can be checked. If it is found that the positioning is not correct, the cryocatheter 2 can simply be pushed a little further or pulled back until the balloon 10 or stent 12, as applicable, is correctly positioned. This is all possible because the imaging sensor 16 is designed, and is arranged at the distal end 6 of the cryocatheter 2, for recording the region of the vessel immediately alongside the balloon 10 or stent 12, as applicable. When the balloon 10 or the stent 12, as applicable, has been correctly positioned, the balloon 10 is then expanded, by means of the expansion and cooling agent K conveyed by the expansion agent pump. The balloon 10 undergoes a defined stretching, the stent 12, which is generally a plastically deformable metal mesh, is uniformly stretched. In doing this, the balloon 10 is blown up far enough for the stent 12 to be roughly fixed to the inner wall of the vessel. At the same time, cryotherapy of the vessel wall surrounding the balloon 10 is effected. After this, the balloon 10 is somewhat deflated again, to enable the position and orientation of the stent 12 to be checked via the image capture device 16. If it is found that the stent 12 is correctly positioned, the balloon 10 is reinflated at a higher pressure, and the stent 12 finally fixed in the vessel 44. After the balloon 10 has been deflated again, a final check can be carried out via the image capture device 16, after which the cryocatheter 2 is pulled out of the vessel 44.

Figure 6:
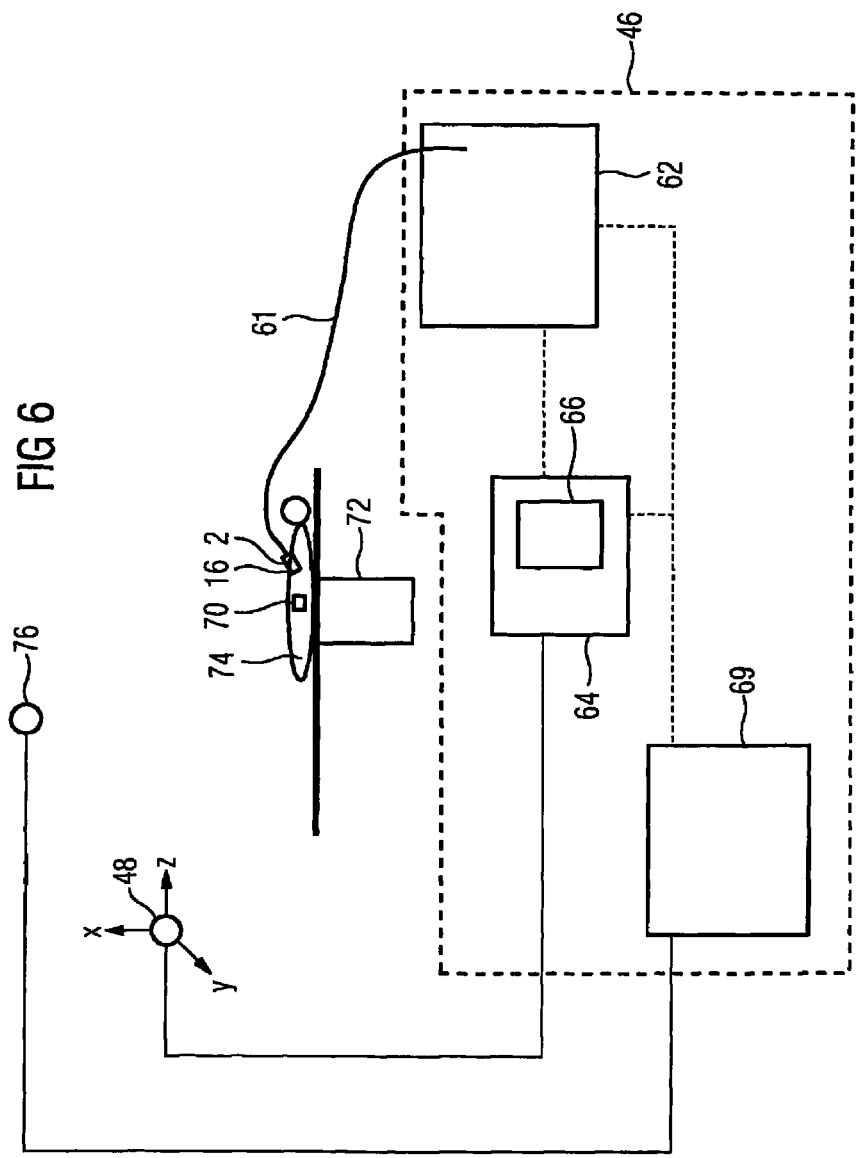
Figure 7:
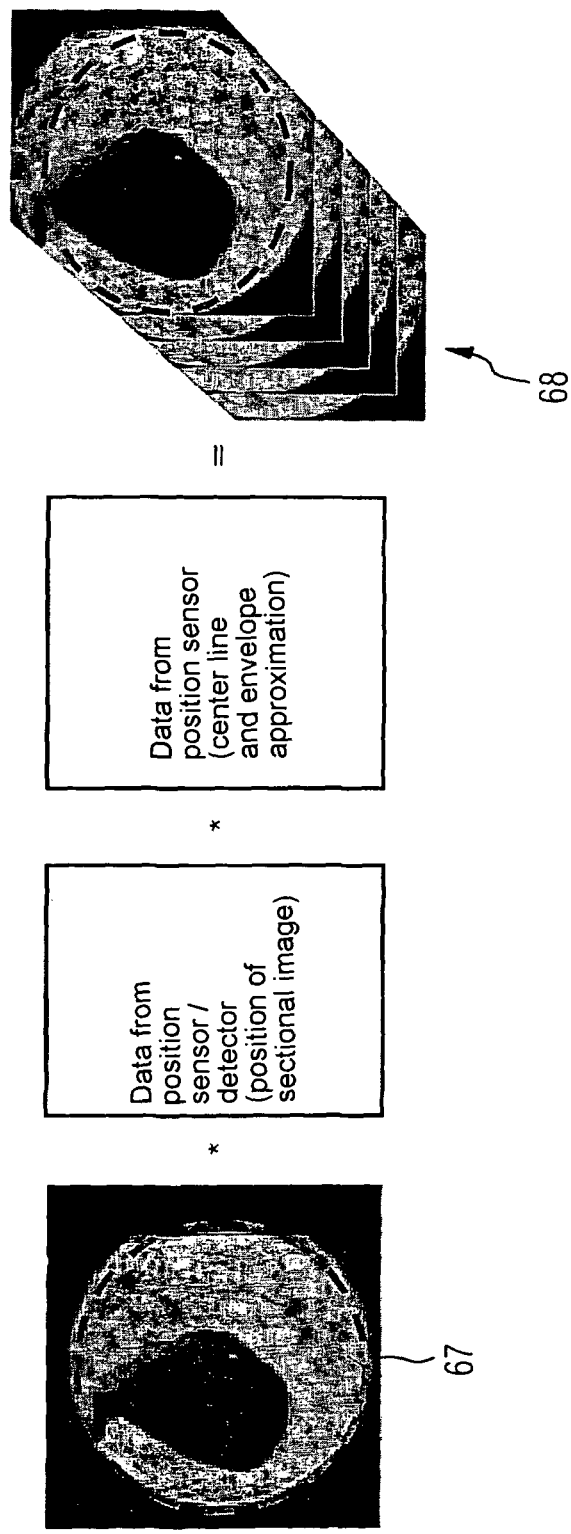
Figure 8:
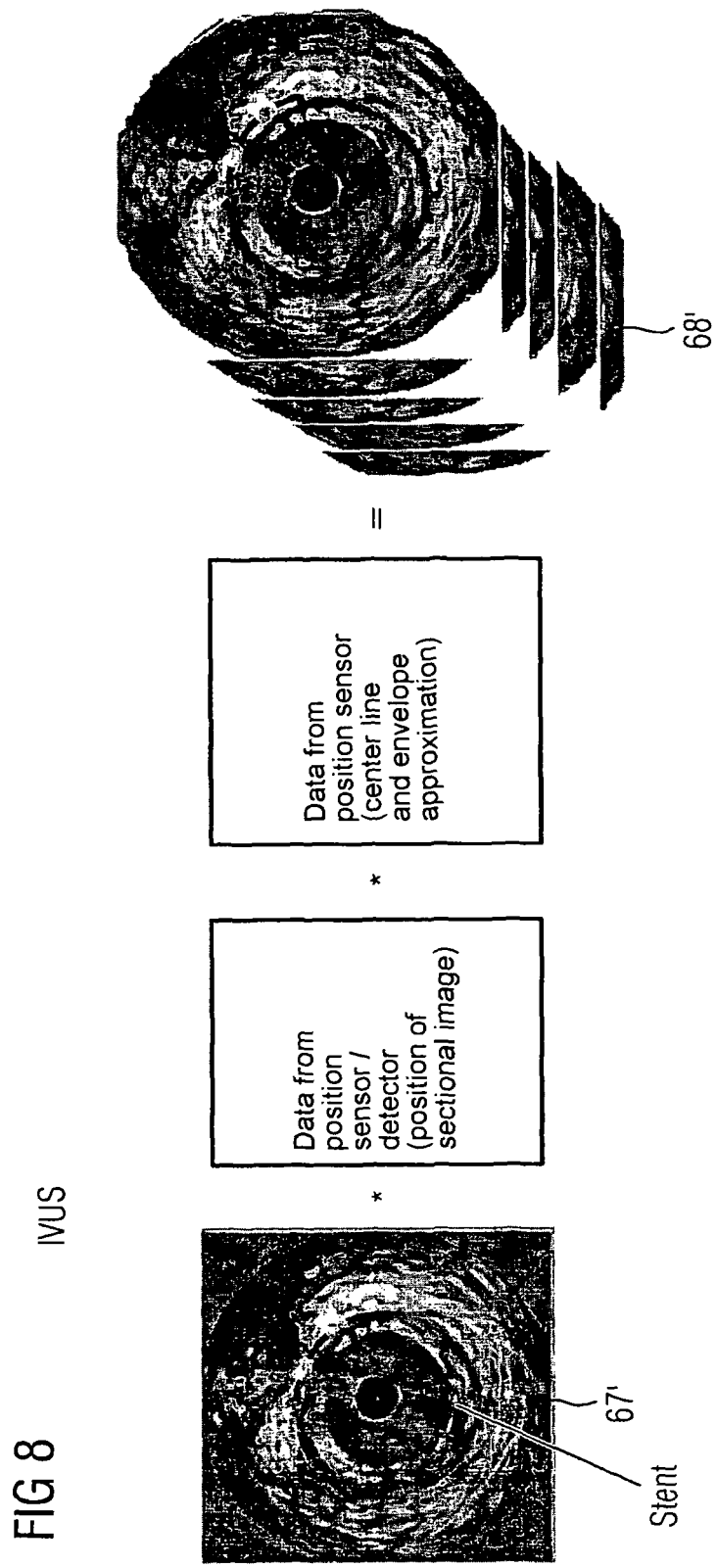
Figure 9:
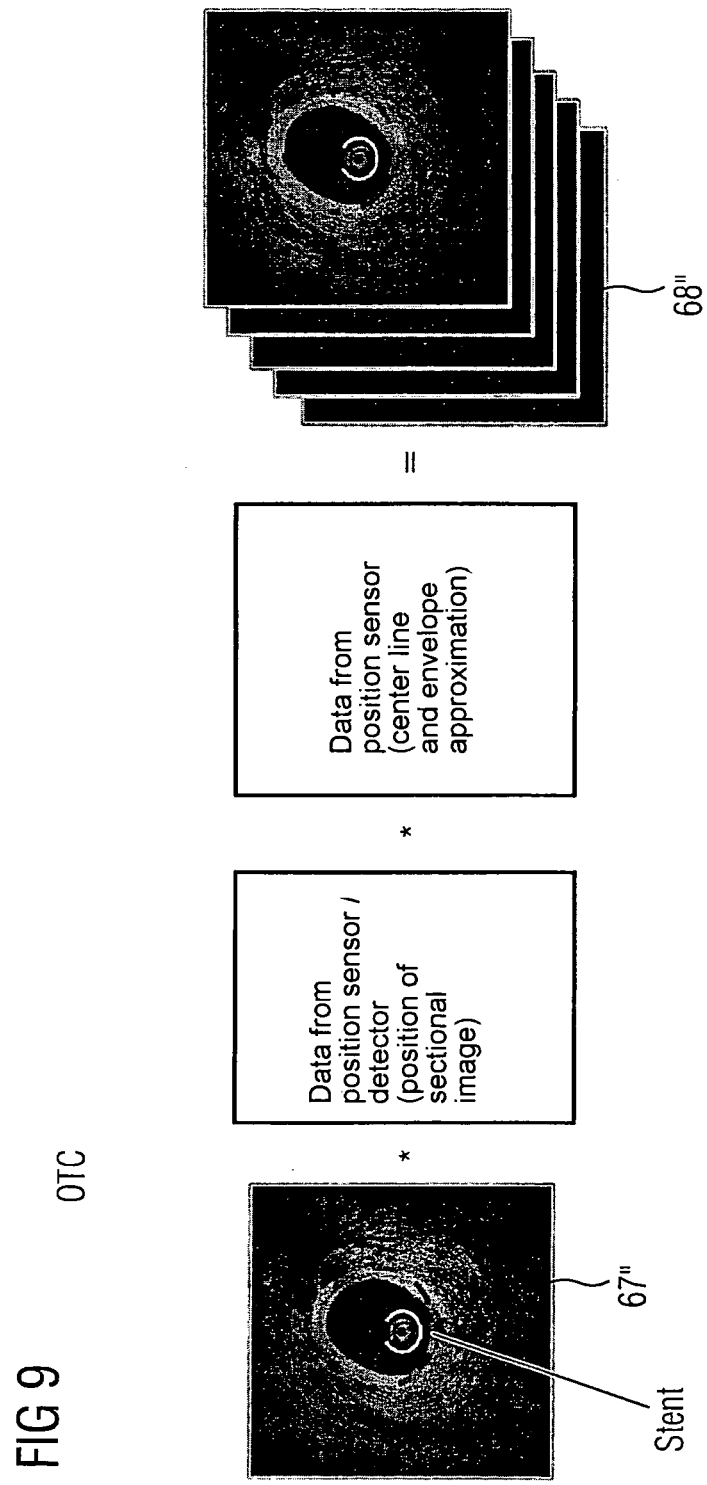
Figure 10:
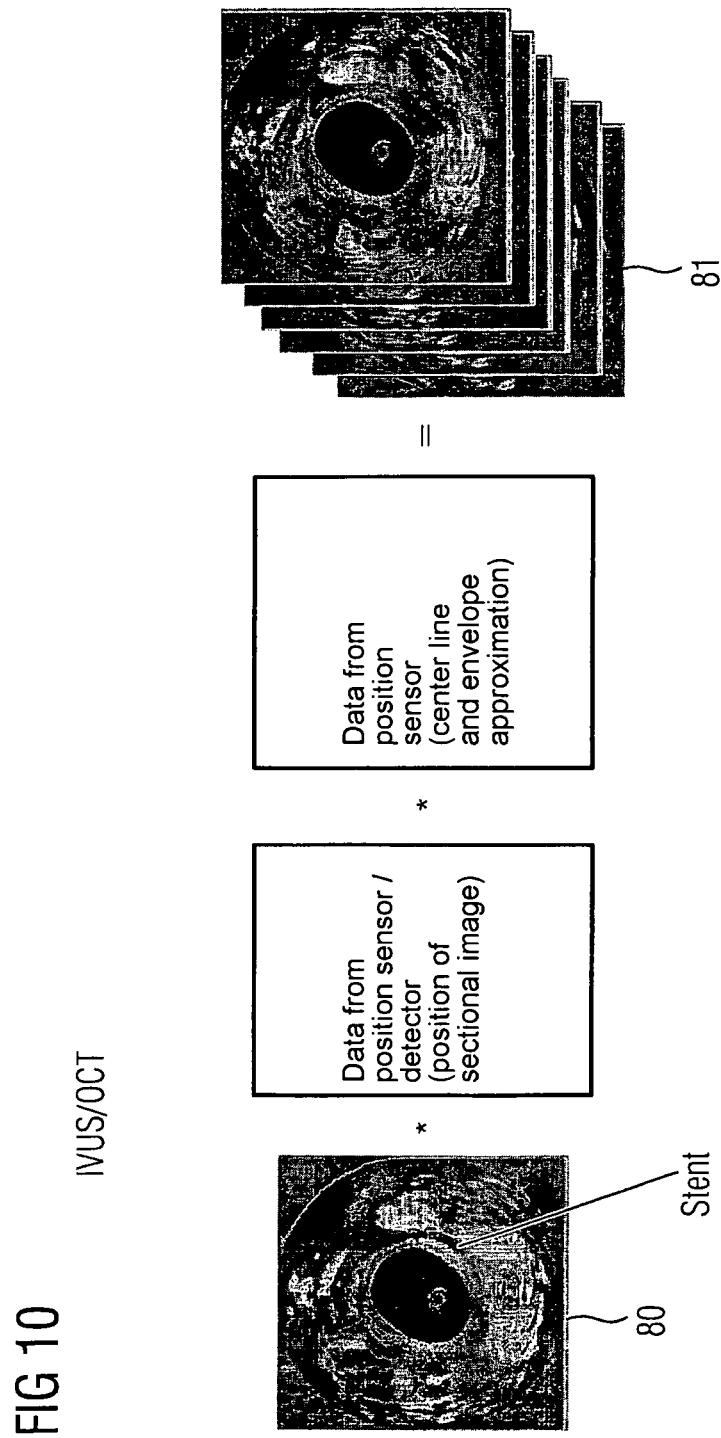

Some further components of the medical investigation and treatment system 42 are shown in FIG. 6, as a schematic sketch. The control and analysis unit 46 includes, apart from a preprocessor 62 in which the sensor signals are appropriately amplified, filtered, digitized and prepared for further digital editing, which is connected to the imaging sensor 16 on the catheter side via a signal line 61, an image processing module 64, in which the actual visualization and posttreatment of the sensor data is effected with the help of facilities implemented by familiar hardware or software facilities. The image processing module 64 incorporates a 3D correction module 66, with a so-called movement and gating processor which, by referring back to the position data for the catheter tip 8 provided by the position signal receiver 48, reconstructs the center line and the envelope of the vessel for the section of the vessel reproduced in the sectional images, and then combines a number of individual images 67, 67', 67" into a reduced-artifact three-dimensional volume dataset 68, 68', 68". This is shown schematically in FIG. 7 to FIG. 9, and indeed separately for IVMRI images (FIG. 7), IVUS images (FIG. 8) and for OCT images (FIG. 9). With the help of the envelope of the vessel and any further applicable geometric parameters of the vessel 44 it is also possible to combine the images, reconstructed three-dimensionally, on a surface basis with other anatomical image data (e.g. 3D angiography, ultrasound) for the same section of the vessel, and then to show this in merged form.

Figure 4:
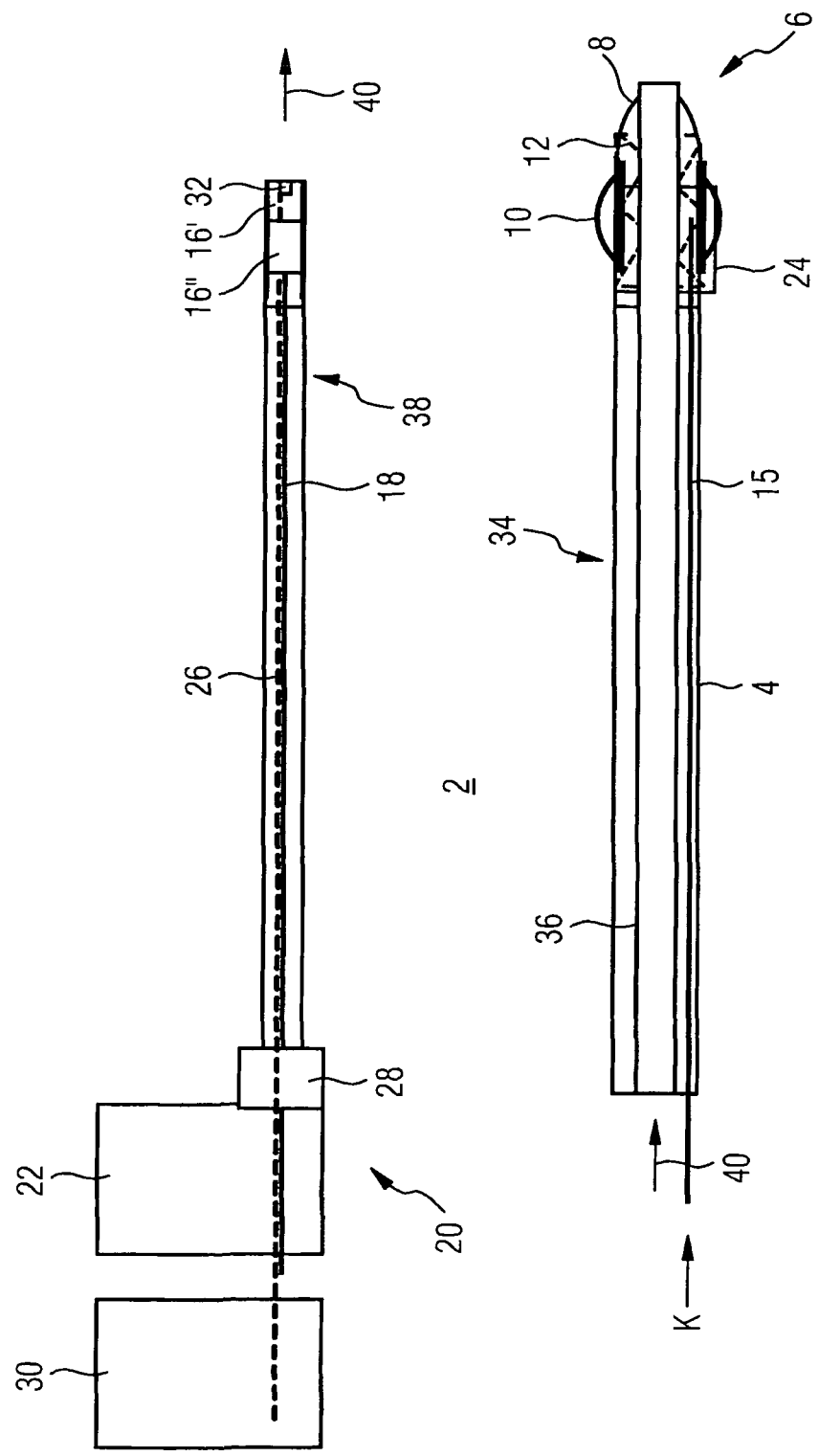

In the case of a cryocatheter 2 with a combined OCT/IVUS sensor (as shown in FIG. 3 or FIG. 4), an image merging unit integrated into the image processing unit 64 serves to generate a common image from the separate images produced respectively using the signals from the OCT sensor or from the IVUS sensor. In the simplest case the "image merging" is merely an overlaying of the individual OCT and IVUS images. However, it is preferable to generate a common combined investigatory image by combining a particular section of the IVUS image with a complementary section of the OCT image to form a common image. The IVUS image has a very good resolution for deeper-lying tissue layers. The OCT image has a very high resolution in the nearby region, making even microscopic images possible. It is appropriate if the two partial images are constructed to be complementary, so that the OCT section fits exactly into the space in the IVUS image. In this way, in generating the combined image use is made of the optimal area of each of the two images. The OCT section of the image and the IVUS section of the image can be blended into each other by means of appropriate image processing programs in such a way that no separating line or contour can be discerned. An example of an IVUS/OCT image 80 which has been blended in this way is shown in FIG. 11. From the two-dimensional images 80 it is again possible to generate three-dimensional reduced-artifact volume datasets 81. The above embodiments can also be applied with appropriate interpretation to other combinations of imaging sensors, e.g. IVUS/IVMRI.

In addition, the intravascular images from the imaging sensor 16 can be overlaid or blended in the image merging unit with the X-ray images from the angiographic X-ray unit 59, or even with earlier records which are already available from other image generation methods (for example CT, MRI, PET or SPECT), which will preferably be provided or communicated, as appropriate, through a DICOM interface.

The 3D correction module 66 shown in FIG. 6 is furthermore linked to a signal interface 69, which has a data link to one or more movement sensors 70 for measuring the breathing movements of the patient 74 held on an examination chair or examination table 72, and to various physiological sensors such as for ECG, pulse, respiration or blood pressure. It is thus also possible to take into account these items of data in the artifact correction of the 3D image. Some of the physiological sensors and the movement sensors 70 take the form of active or passive RFID transponders, and can be read out wirelessly by an RFID reader 76 integrated into the signal interface 69 or connected to it. The RFID transponder concerned will, for example, incorporate an RFID microchip integrated into a plaster, the plaster being stuck onto the skin of the patient during the investigation. The data captured by the movement sensors 70 and the physiological sensors can be displayed on the display monitor of the display unit 52 together with the image data and additional technical data, for example about the phase position or speed of rotation of the imaging sensor 16, or the distance so far moved by the cryocatheter 2. Connected to the display unit 52 or to the analysis and control unit 46 is an input/output unit, I/O unit for short, through which the user can make inputs. In particular, he can influence the display of the image(s) shown on the display monitor. The I/O unit can take the form of a keyboard or an operating console.

In the case of IVMRI imaging, electromagnetic fields which vary with time are generated both by the position sensors 32 and also by the imaging IVMRI sensor 16, and in some circumstances these can affect and distort each other mutually. For the purpose of avoiding such problems, it is proposed that high-frequency MR excitation signals are not emitted continuously but in so-called sequences (clock-pulse controlled), and the position signals from the position sensors 32 are read out with a time offset or synchronously, as appropriate, in such a way that the read-out intervals do not overlap with the generation intervals of the MR signals. This is shown schematically in FIG. 11. In this, the upper graph shows a time-trace of the MR excitation field and the middle graph the response of the excited body tissue, i.e. the MR signal which is used for imaging. Finally, the rectangular-shaped signal windows in the bottom graph represent the time intervals which are favorable for the reading out of the position sensors 32. A readout of the detector signals which has a time offset of this type is appropriate particularly for IVMRI imaging, but it can also be put to use in a similar form with IVUS or OCT imaging.

The invention claimed is:

1. A cryocatheter that inserts into a vessel of a patient in a medical procedure, comprising:
    a catheter sheath;
    a catheter inner side surrounded by the catheter sheath;
    a catheter tip arranged at a distal end of the cryocatheter;
    a feed line arranged in the catheter sheath that feeds an expansion and cooling agent;
    a balloon arranged near the catheter tip that is expanded by the expansion and cooling agent;
    an imaging sensor located near the catheter tip; and
    an image capture device comprising the imaging sensor that maps a region of the vessel around the balloon;
    wherein a stent that is to be implanted in the vessel is arranged on an outside of the balloon, said stent comprising a metallic wire mesh configured to be uniformly stretched beyond an elastic limit upon the expansion of the balloon, so to retain a stretched shape against the vessel; said stent configured to retain said stretched shape subsequent to the balloon having been collapsed, based on the expansion and cooling agent being drained from the balloon;
    wherein the image capture device comprises an IVMRI (intravascular magnetic resonance imaging) sensor and an IVUS (intravascular ultrasonic) sensor or an OCT (optical coherence tomography) sensor and an IVUS (intravascular ultrasonic) sensor that are rotated by a drive shaft;
    and wherein the catheter sheath comprises a window in a region of the imaging sensor that is transparent to an imaging method used by the imaging sensor, and wherein said balloon and said stent are comprised of a material that is transparent to the imaging method used by the imaging sensor.

2. The cryocatheter as claimed in claim 1, wherein the cryocatheter inserts into an organ of the patient.

3. The cryocatheter as claimed in claim 1, wherein the feed line is arranged in the catheter inner side.

4. The cryocatheter as claimed in claim 1,
    wherein the imaging sensor is rotated via the drive shaft that is arranged in the catheter sheath or in the catheter inner side, or
    wherein a plurality of same type imaging sensors are distributed over a cross section of the cryocatheter connected to a common signal line via a multiplexer that is arranged in the catheter sheath or in the catheter inner side, each of the imaging sensors oriented towards a wall of the vessel.

5. The cryocatheter as claimed in claim 1, wherein the cryocatheter is guided by an external magnetic field with a magnetic element arranged in a region of the catheter tip.

6. The cryocatheter as claimed in claim 1, wherein a contrast agent feed line is provided in the catheter sheath or in the catheter inner side and opens to an outlet arranged on an outer side of the catheter sheath.

7. The cryocatheter as claimed in claim 1,
wherein a position sensor is arranged in a region of the catheter tip, and
wherein the position sensor is an electromagnetic sensor or an ultrasonic sensor.

8. The cryocatheter as claimed in claim 7, wherein the cryocatheter comprises:
an outer body that is configured by the catheter sheath and the balloon, and
an inner body that is configured by a plurality of electrical units of the image capture device and the position sensor and is pushed into a cavity of the outer body.

9. The cryocatheter as claimed in claim 8,
wherein the feed line that expands and cools the balloon and a contrast agent feed line are arranged on or in the outer body, and
wherein a plurality of supply and signal lines that link the electrical units to an analysis and control unit and a drive shaft that rotates the image capture device are arranged on or in the inner body.

10. The cryocatheter as claimed in claim 9,
wherein each of the supply and signal lines comprises a protective layer for magnetic screening, and
wherein the electrical units are thermally insulated from the expansion and cooling agent.

11. The cryocatheter as claimed in claim 1, wherein a plurality of X-ray opaque markers are arranged in a region of the catheter tip.

12. The cryocatheter as claimed in claim 1, wherein a technical data about the cryocatheter or a documentation of a usage history of the cryocatheter is stored in an RFID (Radio Frequency Identification) transponder.

* * * * *